US010214294B1

(12) United States Patent
Gauthier et al.

(10) Patent No.: US 10,214,294 B1
(45) Date of Patent: Feb. 26, 2019

(54) METHOD AND SYSTEM FOR PREDICTING POTENTIAL ICING CONDITIONS

(71) Applicant: Blue Storm Associates, Inc., Fairfax Station, VA (US)

(72) Inventors: Michael Gauthier, Castle Rock, CO (US); Brian Griffith, Monument, CO (US); Donna Blake, Oakton, VA (US); Mary Lockhart, Fairfax Station, VA (US)

(73) Assignee: Blue Storm Associates, Inc., Fairfax Station, VA (US)

( * ) Notice: Subject to any disclaimer, the term of this patent is extended or adjusted under 35 U.S.C. 154(b) by 171 days.

(21) Appl. No.: 15/243,188

(22) Filed: Aug. 22, 2016

Related U.S. Application Data

(60) Provisional application No. 62/208,083, filed on Aug. 21, 2015.

(51) Int. Cl.
*G01N 25/56* (2006.01)
*B64D 15/20* (2006.01)

(52) U.S. Cl.
CPC ............. *B64D 15/20* (2013.01); *G01N 25/56* (2013.01)

(58) Field of Classification Search
None
See application file for complete search history.

(56) References Cited

U.S. PATENT DOCUMENTS

| 5,772,153 | A  | * | 6/1998  | Abaunza ................ B64D 15/20 244/134 F |
| 2010/0143127 | A1 | * | 6/2010 | Ahmann ................. F03D 80/40 416/61 |
| 2012/0099616 | A1 | * | 4/2012 | Penny .................... B64D 15/20 374/16 |
| 2014/0192356 | A1 | * | 7/2014 | Antikainen ............. G01S 17/58 356/342 |
| 2015/0339930 | A1 | * | 11/2015 | McCann .............. G08G 5/0039 701/528 |
| 2016/0221680 | A1 | * | 8/2016 | Burton ................... B64D 15/12 |
| 2017/0045404 | A1 | * | 2/2017 | Fuleki .................. G01K 13/028 |
| 2017/0174365 | A1 | * | 6/2017 | Luca ........................ B64F 5/23 |
| 2017/0229021 | A1 | * | 8/2017 | McCann .............. G08G 5/0039 |

OTHER PUBLICATIONS

Air Weather Service, 1980: Forecaster's Guide on Aircraft Icing. Air Weather Service (MAC) Tech. Rep. AWS/TR-80/001, Scott AFB, IL, 60 pgs.

(Continued)

*Primary Examiner* — Andre J Allen
(74) *Attorney, Agent, or Firm* — Davidson Berquist Jackson & Gowdey, LLP

(57) ABSTRACT

A method and system for predicting the potential for icing conditions on an outer surface of an airborne aircraft. Such a method and system may predict in real-time the potential for icing conditions on an outer surface of a wing of an autonomous airborne aircraft using observed temperature and relative humidity measurements, either jointly, or also in combination with at least one of (1) an output from at least one additional sensor relevant to the prediction of aircraft icing conditions and (2) a modeled parameter relevant to the prediction of aircraft icing conditions.

20 Claims, 6 Drawing Sheets

(56) References Cited

OTHER PUBLICATIONS

Appleman, H., 1954: Design of a cloud-phase chart. Bull. Amer. Meteor. Soc., 35, 223-225.

Bernstein, B. C., C. A. Wolff, and F. McDonough, 2007: An Inferred Climatology of Icing Conditions Aloft, Including Supercooled Large Drops. Part I: Canada and the Continental United States. Journal of Applied Meteorology and Climatology, 46, 1857-1878, doi:10.1175/2007JAMC1607.1.

Bernstein, B. C., F. McDonough, M. K. Politovich, B. G. Brown, T. P. Ratvasky, D. R. Miller, C. A. Wolff, and G. Cunning, 2005: Current icing potential: Algorithm description and comparison with aircraft observations. Journal of Applied Meteorology, 44, 969-986.

Brown, B. G. et al., 1997: Intercomparison of In-Flight Icing Algorithms. Part II: Statistical Verification Results, Weather and Forecasting, vol. 12, American Meteorological Society, 890-914 (Brown 1997).

Dennstaedt, S. C., 2006: The Appleman Line. IFR Magazine, vol. 22, Iss. 2, pp. 6-8, 23.

Gregory Thompson, Roelof T. Bruintjes, Barbara G. Brown, and Frank Hage, 1997: Intercomparison of In-Flight Icing Algorithms. Part I: WISP94 Real-Time Icing Prediction and Evaluation Program. Wea. Forecasting, 12, 878-889.

Politovich, M. K., and T. A. Bernstein, 2002: Aircraft icing conditions in northeast Colorado. Journal of Applied Meteorology, 41, 118-132.

Schultz, P., and M. K. Politovich, 1992: Toward the Improvement of Aircraft-Icing Forecasts for the Continental United States. Weather and Forecasting, 7, 491-500, doi:10.1175/1520-0434(1992)007<0491:TTIOAI>2.CO;2.

Tremblay, A., S. G. Cober, A. Glazer, G. Isaac, and J. Mailhot, 1996: An intercomparison of mesoscale forecasts of aircraft icing using SSM/I retrievals, Weather and forecasting, 11, 66-77.

\* cited by examiner

FIG. 3A

| Temperature (Deg F) | Icing Possible |
|---|---|
| 0 | 0.1 |
| -1 | 0.15 |
| -2 | 0.2 |
| -3 | 0.25 |
| -4 | 1 |
| -5 | 1 |
| -6 | 1 |
| -7 | 1 |
| -8 | 1 |
| -9 | 0.98 |
| -10 | 0.94 |
| -11 | 0.89 |
| -12 | 0.78 |
| -13 | 0.68 |
| -14 | 0.58 |
| -15 | 0.5 |
| -16 | 0.42 |
| -17 | 0.36 |
| -18 | 0.3 |
| -19 | 0.23 |
| -20 | 0.17 |
| -21 | 0.13 |
| -22 | 0.1 |
| -23 | 0.075 |
| -24 | 0.05 |
| -25 | 0.03 |
| -26 | 0.01 |
| -27 | 0.005 |
| -28 | 0.0025 |
| -29 | 0.001 |
| -30 | 0 |

FIG. 3B

| Dewpoint Depression (Deg F) | Icing Possible |
|---|---|
| 31 | 0 |
| 32 | 0.01 |
| 33 | 0.01 |
| 34 | 0.01 |
| 35 | 0.02 |
| 36 | 0.02 |
| 37 | 0.03 |
| 38 | 0.03 |
| 39 | 0.03 |
| 40 | 0.04 |
| 41 | 0.04 |
| 42 | 0.04 |
| 43 | 0.05 |
| 44 | 0.05 |
| 45 | 0.05 |
| 46 | 0.06 |
| 47 | 0.06 |
| 48 | 0.06 |
| 49 | 0.07 |
| 50 | 0.07 |
| 51 | 0.08 |
| 52 | 0.08 |
| 53 | 0.08 |
| 54 | 0.09 |
| 55 | 0.095 |
| 56 | 0.1 |
| 57 | 0.1 |
| 58 | 0.1 |
| 59 | 0.11 |
| 60 | 0.11 |
| 61 | 0.12 |
| 62 | 0.13 |
| 63 | 0.13 |
| 64 | 0.14 |
| 65 | 0.15 |
| 66 | 0.17 |
| 67 | 0.19 |
| 68 | 0.2 |
| 69 | 0.22 |
| 70 | 0.24 |
| 71 | 0.26 |
| 72 | 0.28 |
| 73 | 0.3 |
| 74 | 0.32 |
| 75 | 0.34 |
| 76 | 0.36 |
| 77 | 0.39 |
| 78 | 0.41 |
| 79 | 0.44 |
| 80 | 0.46 |
| 81 | 0.49 |
| 82 | 0.52 |
| 83 | 0.55 |
| 84 | 0.58 |
| 85 | 0.61 |
| 86 | 0.64 |
| 87 | 0.68 |
| 88 | 0.71 |
| 89 | 0.75 |
| 90 | 0.78 |
| 91 | 0.82 |
| 92 | 0.87 |
| 93 | 0.91 |
| 94 | 0.96 |
| 95 | 1 |
| 96 | 1 |
| 97 | 1 |
| 98 | 1 |
| 99 | 1 |
| 100 | 1 |

| Forecast | Observation | | Total |
|---|---|---|---|
| | YES | NO | |
| YES | YY | YN | YY+YN |
| NO | NY | NN | NY+NN |
| Total | YY+NY | YN+NN | YY+YN+ NN+NY |

Fig. 4 - 2 x 2 Contingency Table

| Time | Temperature (degrees C) | Relative Humidity (Percent) | RH$_{avg}$ | T$_{avg}$ | B-TIP(%) [T$_{avg}$ x RH$_{avg}$] | Threat |
|---|---|---|---|---|---|---|
| 17:42:08 | 15 | 30 | 0 | 0 | 0 | NONE |
| 17:42:19 | 15 | 29 | 0 | 0 | 0 | NONE |
| 17:42:33 | 15 | 29 | 0 | 0 | 0 | NONE |
| 17:42:40 | 16 | 29 | 0 | 0 | 0 | NONE |
| 17:42:50 | 15 | 29 | 0 | 0 | 0 | NONE |
| ⋮ | ⋮ | ⋮ | | | | ⋮ |
| 19:11:24 | -2 | 63 | 0.13 | 0.80 | 0.10 | MED |
| 19:11:34 | -2 | 63 | 0.13 | 0.80 | 0.10 | MED |
| 19:11:44 | -1 | 63 | 0.13 | 0.35 | 0.05 | MED |
| 19:11:55 | -1 | 62 | 0.13 | 0.35 | 0.05 | MED |
| 19:12:06 | -2 | 62 | 0.13 | 0.80 | 0.10 | MED |
| 19:12:17 | -2 | 63 | 0.13 | 0.80 | 0.10 | MED |
| 19:12:27 | -2 | 63 | 0.13 | 0.80 | 0.10 | MED |
| 19:12:37 | -2 | 64 | 0.14 | 0.80 | 0.11 | MED |
| 19:12:48 | -2 | 66 | 0.17 | 0.80 | 0.14 | MED |
| 19:12:58 | -2 | 66 | 0.17 | 0.80 | 0.14 | MED |
| 19:13:09 | -2 | 67 | 0.19 | 0.80 | 0.15 | HIGH |
| 19:13:20 | -2 | 67 | 0.19 | 0.80 | 0.15 | HIGH |
| 19:13:30 | -2 | 68 | 0.20 | 0.80 | 0.16 | HIGH |
| 19:13:41 | -2 | 68 | 0.20 | 0.80 | 0.16 | HIGH |
| 19:13:51 | -2 | 68 | 0.20 | 0.80 | 0.16 | HIGH |
| 19:14:02 | -2 | 67 | 0.19 | 0.80 | 0.15 | HIGH |
| 19:14:12 | -2 | 67 | 0.19 | 0.80 | 0.15 | HIGH |
| 19:14:23 | -2 | 68 | 0.20 | 0.80 | 0.16 | HIGH |
| 19:14:35 | -2 | 68 | 0.20 | 0.80 | 0.16 | HIGH |
| 19:14:45 | -2 | 69 | 0.22 | 0.80 | 0.18 | HIGH |
| 19:14:56 | -2 | 68 | 0.20 | 0.80 | 0.16 | HIGH |
| 19:15:08 | -2 | 70 | 0.24 | 0.80 | 0.19 | HIGH |
| 19:15:19 | -2 | 70 | 0.24 | 0.80 | 0.19 | HIGH |
| 19:15:30 | -2 | 71 | 0.26 | 0.80 | 0.21 | HIGH |
| 19:15:42 | -2 | 70 | 0.24 | 0.80 | 0.19 | HIGH |
| 19:15:52 | -2 | 70 | 0.24 | 0.80 | 0.19 | HIGH |
| 19:16:03 | -2 | 70 | 0.24 | 0.80 | 0.19 | HIGH |
| 19:16:13 | -2 | 70 | 0.24 | 0.80 | 0.19 | HIGH |
| 19:16:24 | -2 | 70 | 0.24 | 0.80 | 0.19 | HIGH |
| 19:16:34 | -2 | 70 | 0.24 | 0.80 | 0.19 | HIGH |
| 19:16:45 | -2 | 70 | 0.24 | 0.80 | 0.19 | HIGH |
| 19:16:56 | -2 | 69 | 0.22 | 0.80 | 0.18 | HIGH |
| 19:17:06 | -2 | 69 | 0.22 | 0.80 | 0.18 | HIGH |
| 19:17:17 | -2 | 68 | 0.20 | 0.80 | 0.16 | HIGH |
| 19:17:27 | -1 | 68 | 0.20 | 0.35 | 0.07 | MED |
| 19:17:38 | -1 | 69 | 0.22 | 0.35 | 0.08 | MED |
| 19:17:48 | -1 | 68 | 0.20 | 0.35 | 0.07 | MED |
| 19:17:58 | -1 | 68 | 0.20 | 0.35 | 0.07 | MED |
| ⋮ | ⋮ | ⋮ | | | | ⋮ |
| 19:43:54 | 5 | 56 | 0.09 | 0.00 | 0.00 | NONE |
| 19:44:05 | 5 | 56 | 0.09 | 0.00 | 0.00 | NONE |
| 19:44:15 | 5 | 55 | 0.09 | 0.00 | 0.00 | NONE |
| 19:44:25 | 5 | 55 | 0.09 | 0.00 | 0.00 | NONE |
| 19:44:36 | 5 | 56 | 0.09 | 0.00 | 0.00 | NONE |

FIG. 7

METHOD AND SYSTEM FOR PREDICTING POTENTIAL ICING CONDITIONS

CROSS-REFERENCE TO RELATED APPLICATIONS

This application claims priority to provisional U.S. Patent Application No. 62/208,083, filed Aug. 21, 2015, the contents of which are incorporated by reference.

FIELD OF INVENTION

The present invention is directed to a method and system for detecting the potential for icing conditions (i.e., predicting that icing will occur under measured conditions) on an outer surface of an airborne aircraft, and, in one embodiment, for detecting in real-time the potential for icing conditions on an outer surface of a wing of an autonomous airborne aircraft.

DISCUSSION OF THE BACKGROUND

A number of aircraft icing threat identification algorithms based on modeled conditions, as opposed to observed measurements are known. See, e.g., (1) Air Weather Service, 1980: Forecaster's Guide on Aircraft Icing. Air Weather Service (MAC) Tech. Rep. AWS/TR-80/001, Scott AFB, IL, 55 pp; (2) Appleman, H., 1954: Design of a cloud-phase chart. Bull. Amer. Meteor. Soc., 35, 223-225; (3) Bernstein, B. C., F. McDonough, M. K. Politovich, B. G. Brown, T. P. Ratvasky, D. R. Miller, C. A. Wolff, and G. Cunning, 2005: Current icing potential: Algorithm description and comparison with aircraft observations. Journal of Applied Meteorology, 44, 969-986; (4) Bernstein, B. C., C. A. Wolff, and F. McDonough, 2007: An Inferred Climatology of Icing Conditions Aloft, Including Supercooled Large Drops. Part I: Canada and the Continental United States. Journal of Applied Meteorology and Climatology, 46, 1857-1878, doi: 10.1175/2007JAMC1607.1; (5) Brown, B. G. et al., 1997: Intercomparison of In-Flight Icing Algorithms. Part II: Statistical Verification Results, Weather and Forecasting, Vol. 12, American Meteorological Society, 890-914 (Brown 1997); (6) Bruintjes, R. T., B. G. Brown, J. Coen, G. Thompson, and T. L. Kane, 2003: Final report on development of icing potential product, NCAR/RAP Report to Phillips Laboratory. 190 pp (Brown 2003); (7) Dennstaedt, S. C., 2006: The Appleman Line. IFR Magazine, Vol. 22, Iss. 2, pp. 6-8, 23; (8) Politovich, M. K., and T. A. Bernstein, 2002: Aircraft icing conditions in northeast Colorado. Journal of Applied Meteorology, 41, 118-132; (9) Schultz, P., and M. K. Politovich, 1992: Toward the Improvement of Aircraft-Icing Forecasts for the Continental United States. Weather and Forecasting, 7, 491-500, doi:10.1175/1520-0434(1992)007<0491:TTIOAI>2.0.CO;2.; (10) Gregory Thompson, Roelof T. Bruintjes, Barbara G. Brown, and Frank Hage, 1997: Intercomparison of In-Flight Icing Algorithms. Part I: WISP94 Real-Time Icing Prediction and Evaluation Program. Wea. Forecasting, 12, 878-889; and (11) Tremblay, A., S. G. Cober, A. Glazer, G. Isaac, and J. Mailhot, 1996: An intercomparison of mesoscale forecasts of aircraft icing using SSM/I retrievals, Weather and forecasting, 11, 66-77. Each of those references is incorporated herein by reference.).

BRIEF DESCRIPTION OF THE DRAWINGS

The following description, given with respect to the attached drawings, may be better understood with reference to the non-limiting examples of the drawings, wherein:

FIGS. 3A and 3B are temperature and relative humidity interest maps, respectively, for detecting the potential for icing conditions on an outer surface of an airborne aircraft, wherein, when multiplied together, the maps define the joint probability space that represents the potential for icing to occur based solely on temperature and relative humidity;

FIG. 4 is a 2 by 2 contingency table;

FIG. 7 is a subset of the data used to calculate the graph of FIG. 6.

DISCUSSION OF THE PREFERRED EMBODIMENTS

As disclosed herein, a system and method diagnose the potential of in-flight icing events, either in a delayed mode or in a real-time mode. The real-time mode is indicated as R-TIP (Real-Time Icing Potential), but the same system and method acting in R-TIP mode can also be operated in a delayed mode. The system and method combine in-situ sensor measurements (e.g., measures of atmospheric temperature and relative humidity and optionally sensor outputs from other additional sensors relevant to the prediction or verification of icing and/or modeled parameters) with an analysis system (e.g., tailored fuzzy-logic membership functions relative to each observable) to create (e.g., in real-time) an icing prediction (i.e., a determination of the potential for the occurrence of structural aircraft icing). The aircraft can be locally- or remotely-piloted and can be any aircraft, such as an airplane or a helicopter. The system and method can utilize either separate temperature and relative humidity sensors or can use a combined temperature and relative humidity sensor (e.g., the sensor disclosed in co-pending U.S. application Ser. No. 14/264,266, filed Apr. 29, 2014). The system and method generate an icing threat index (ITI) at a specified frequency where the ITI output is based on the frequency of observations. In one embodiment, the ITI is output is once per second and provided via a downlink to operators and flight controllers for use in decision making process to assure resource protection of the airborne platform. In one embodiment, the ITI is calculated more frequently than it is output/transmitted, and in another embodiment, the ITI is calculated at the frequency that the ITI is output/transmitted. Additionally, the system and method can incorporate output data from additional sensors resident on the aircraft and relevant to the determination of icing conditions. Examples include, but are not limited to, analog ice prediction systems that provide positive indications when icing is present.

Figure 1:
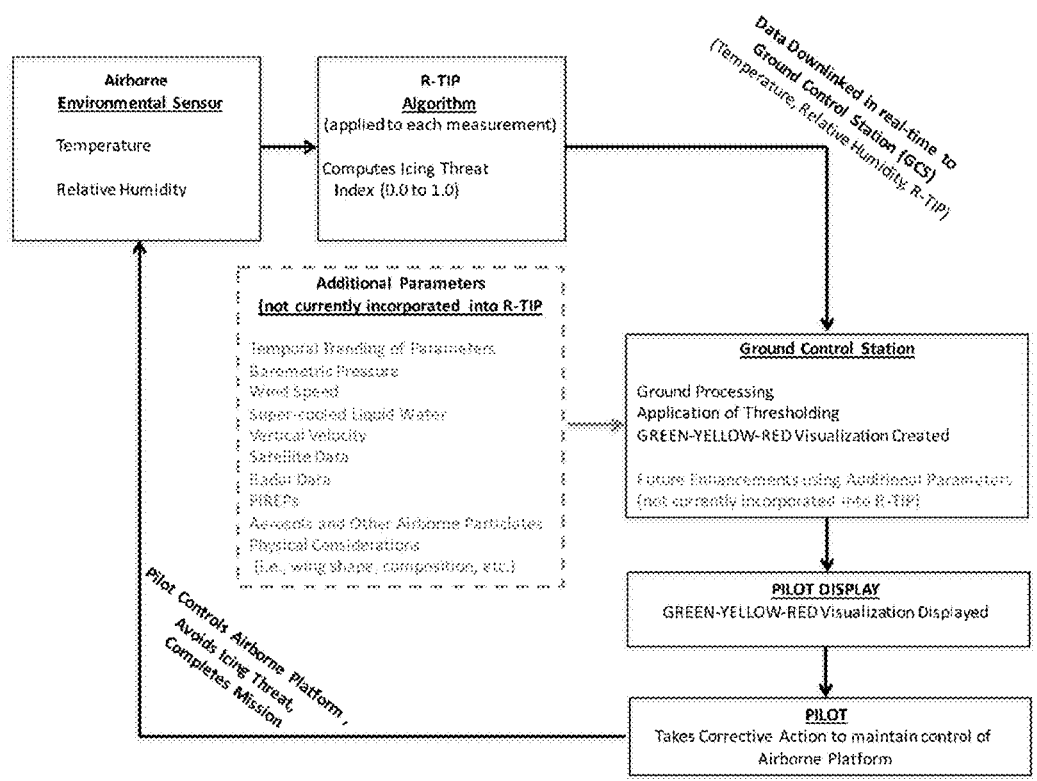
FIG. 1 is block diagram depicting dataflow, processing, and actions associated with detecting the potential for icing conditions on an outer surface of an airborne aircraft.

As shown in FIG. 1, the sensor information is acquired while the aircraft is airborne, and the sensor information is passed to the method and system described herein. Additionally, output data from additional sensors resident on the aircraft and relevant to the determination of icing conditions may be received and processed by the method and system.

The method and system may be in the form of an on-board processor and memory that interface with the sensor(s) as well as special purpose code that implement the functions described herein. Alternatively, the method and system may be implemented as a system on a chip, an ASIC (application specific integrated circuit) or other reprogrammable circuitry (e.g., GAL, FPGA) that interface with the sensor(s) and implement the functions described herein. The method and system calculate the ITI (e.g., in the range of 0.0 to 1.0). In the case of unmanned or remotely piloted aircraft, in one embodiment, the ITI is sent to remote operators and/or flight controllers (e.g., at a ground control station (GCS)), potentially with other information from other sensors (e.g., GPS data). In piloted aircraft, the ITI information may be provided directly to the local pilot/navigator. The ITI information is presented to the operators, flight controllers or pilot/navigator on a display and/or in audio format. When presented on a display, the ITI may be presented as either a number (e.g., in the range of 0.0 to 1.0 or 0 to 10), or in a graphical format (e.g., green for low probability of icing, yellow for increased probability of icing and red for high or imminent probability of icing). Further, indications from additional sensors resident on the aircraft and relevant to the prediction (and detection) of icing may be displayed to the local and remote pilot. The local or remote pilot may then take action based on the ITI or its graphical or audio format, as well as the indications from other icing-relevant sensors. In the case of unmanned or remotely piloted aircraft, in another embodiment, the sensor data may be sent to a computer system of the remote operators and/or flight controllers instead such that the sensor information is converted to an ITI on the computer system of the remote operators and/or flight controllers. This sensor information may also be merged with additional sensor output and/or other observed or modeled meteorological parameters relevant to the prediction of icing conditions (e.g., cloud top temperatures and/or direction and magnitude of vertical motion of the atmosphere) to provide the pilot warnings and advisories. It would be appreciated by those of ordinary skill in the art that vertical motion upwards in the atmosphere increases the potential for icing while vertical motion downwards decreases the potential for icing, and vertical motion can be indicated by either speed measurements (e.g., m/s), such as those taken by GPS, or pressure measurements (microbars/s).

Based on quantitative analysis of nearly 4.3 million point observations, the method and system use a physically based situational approach to estimate the potential for the existence of super-cooled liquid water capable of enabling the accumulation of ice on an aircraft enveloped within a given airspace. The icing potential values range from 0.0 to 1.0; although not calibrated as true probabilities, high (low) values indicate a relatively high (low) chance for the occurrence of icing.

In one embodiment, the method and system use fuzzy-logic membership functions to develop interest maps for the temperature and relative humidity fields. Rather than applying strict thresholds, the method and system handle uncertainties evident in the individual datasets by merging the relative potentials of each individual observable into a joint-potential, one that mimics the gradual transition from icing to non-icing environments. A temperature interest map (e.g., FIG. 3A) indicates the likelihood of super-cooled liquid water that may freeze onto an aircraft, given only observations of in-situ temperature. Similarly, a relative humidity interest map (e.g., FIG. 3B) indicates the likelihood of icing based on observations of this parameter alone.

The final ITI is determined by combining the relative likelihoods associated with each observed field (e.g., temperature and relative humidity and/or other sensor and/or predicted information). Such a combination is preferably in the form of a multiplication of their respective values. When the values of FIGS. 3A and 3B (for temperature and relative humidity) are multiplied together, it generates the ITI which represents the potential for aircraft icing to occur based jointly on the temperature and relative humidity values. A probability value of 0.0 is associated with temperature and relative humidity values that are not favorable for the occurrence of structural icing, and those 0.0 values need not be stored in the tables. Relative humidity is also restricted to the range of 0 to 100%. The resulting ITI has a range of 0.0 to 1.0, where 0.0 is a low probability of icing and 1.0 is a high probability of icing.

In alternate embodiments, the above-fuzzy logic schema can be supplemented with or replaced by alternate individual lookup tables, neural networking technologies and other decision tree technologies. Additionally, the input parameters are not restricted to only temperature and relative humidity. Additional real-time and/or post processor derived observables can also be used. Additional parameters include observations of: pressure, wind speed, super-cooled liquid water, vertical velocities, Pilot Reports (PIREPs), radar reflectivity, cloud top temperatures, GPS winds, and other physical and/or thermodynamic measures of the atmosphere and its constituents (i.e., aerosols and other particulate matter). Additionally, temporal trending information of current and future parameters can likewise be used. Other factors that may change temperature also may be tracked, such as whether a wing is being heated, by how much and for how long. Other parameters that may be tracked include barometric pressure, winds, aerosols, as well as any number of chemical, biological, radiological, and environmental airborne particles. Further, the output from additional aircraft icing sensors may be incorporated in the logic for processing.

Figure 2:
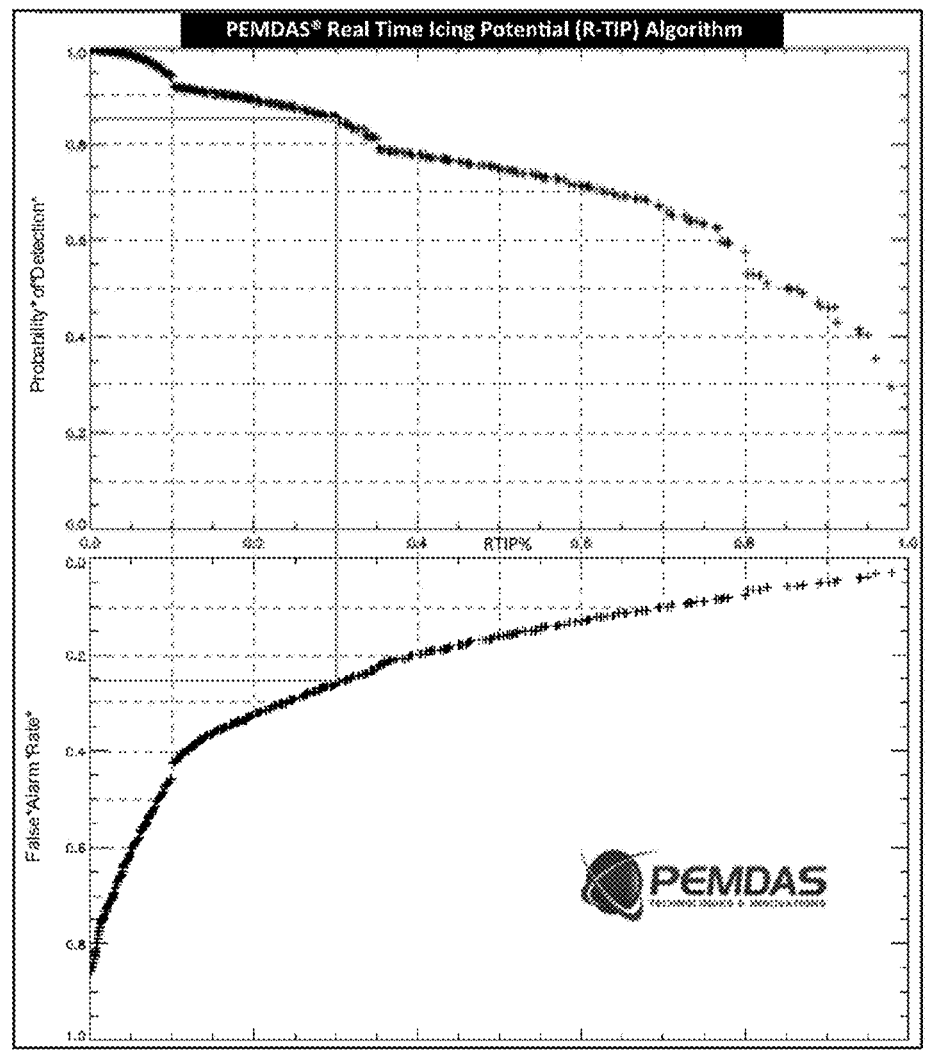
FIG. 2 is a graphical user interface for selecting a threshold to use for detecting the potential for icing conditions on an outer surface of an airborne aircraft.

As shown in FIG. 2, a threshold selection tool enables a threshold to be specified based on observed data. Nearly 4.3 million point observations of icing and non-icing events were used to quantify the probability of detection and false alarm rates. The composite dataset used in the development of the system and method (including the selection tool) included 4,274,860 point observations of temperature and relative humidity, each with a binary (yes/no) icing classification associated with it. Thus, each threshold is accompanied by statistics that describe the probability of detection and false alarm rate.

Matching Methods

Methods used to connect binary icing classifications (i.e., observations) derived from the composite dataset with output from the method and system follow those used to connect PIREPs with other in-flight icing algorithms. Because the method and system provide a continuous measure of icing potential, a threshold was applied to the output of the method and system to obtain YES and NO icing predictions. A variety of thresholds were applied to the predictions, with verification statistics computed for each threshold.

Verification Approach

A 2×2 contingency table (see FIG. 4) was used to generate the statistics of interest (as described below). The primary verification statistics of interest include the following:

PODy=Probability of Detecting a YES icing event [YY/(YY+NY); FIG. 4]; the proportion of positive icing events that were correctly predicted to be in locations with icing conditions. PODy ranges from 0 to 1, with 1 the "best" outcome;

PODn=Probability of Detecting a NO icing event [NN/(NN+YN); FIG. 4]; the proportion of negative icing events that were correctly predicted to be in locations with no icing conditions. PODn ranges from 0 to 1, with 1 the "best" outcome.

FAR=False Alarm Rate; equivalent to '1-PODn', which ranges from 0 to 1, with 0 being the "best" outcome;

TSS=True Skill Statistic (Hanssen-Huipers discrimination) [PODy+PODn-1]; the level of discrimination between YES and NO observations. TSS ranges from -1 to +1, with +1 being the "best", and 0 indicating "no skill".

Together, PODy and PODn measure the ability of the system to discriminate between (or correctly categorize) YES and NO icing observations. This discrimination ability is summarized by the True Skill Statistic (TSS), which frequently is called the Hanssen-Kuipers discrimination statistic (Wilks, 1995). It is possible to obtain the same value of TSS for a variety of combinations of PODy and PODn, thus, PODy, PODn, and TSS should be collectively considered.

The relationship between PODy and FAR (1-PODn') for different thresholds is the basis for a verification approach known as "Signal Detection Theory" (SDT). For a given algorithm or system, this relationship can be represented by the curve joining the (FAR, PODy) points for different algorithm thresholds. The resulting curve is known as a "Relative Operations Characteristic" (ROC) curve in SDT. ROC curves measure the skill of a set of predictions at discriminating between YES and NO observations.

As in previous icing verification analyses (referenced above), emphasis is placed on PODy, PODn, and FAR. Use of this combination of statistics implies that the underlying goal of the algorithm development is to maximize the correct classification of YES and NO icing predictions based on (observed/in-situ) input parameters.

Figure 5:
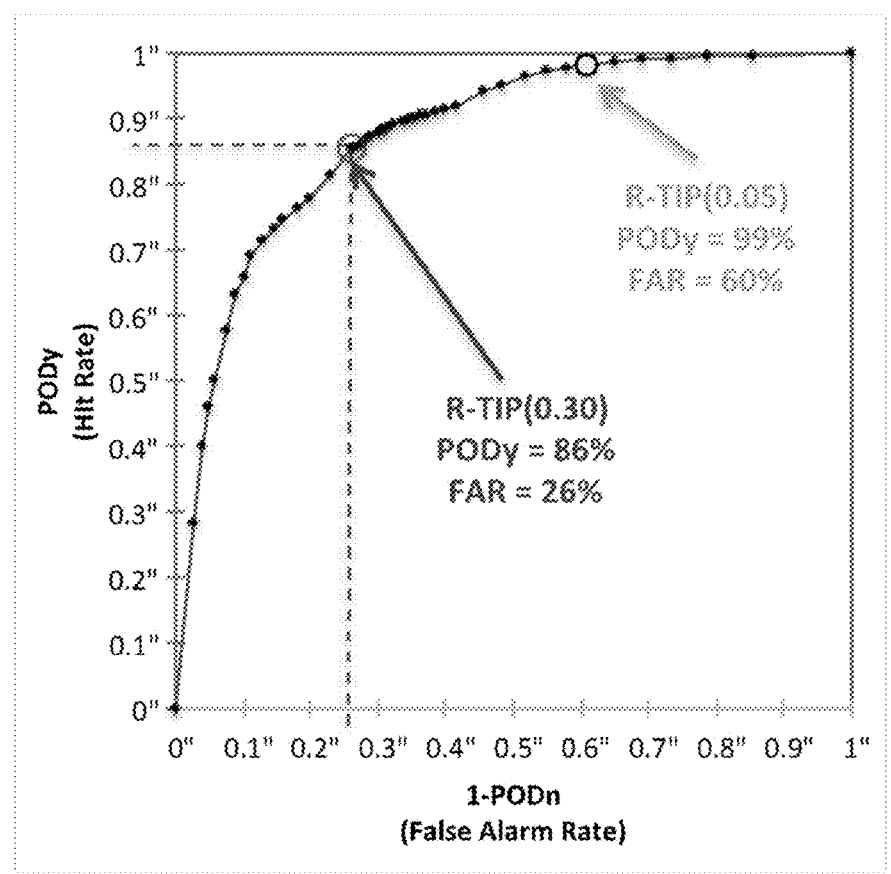
FIG. 5 is a relative operating characteristics (ROC) curve showing a relationship between Probability of Detecting a YES icing event (PODy) and a False Alarm Rate (FAR)

FIG. 5 shows the relationship between PODy and FAR (i.e., the ROC diagram) based on application of the method and system to the composite dataset. This diagram measures the trade-off between correct classification of YES observations and incorrect classification of NO observations. Here, statistics for better predictions are located further toward the upper left corner of the diagram. Results in FIG. 5 indicate that the method and system have positive skill with respect to this combination of verification statistics. Examining the results of the method and system at an "optimal" threshold value of 0.3 (the threshold value associated with the maximum TSS, the one that maximizes the discrimination of both YES and NO events), the method and system yield a PODy of 0.86 with an associated PODn of 0.74 (a 26% false alarm rate), indicating that at this threshold it is able to correctly classify 86% of the YES and 74% of the NO icing events; TSS=0.59 for this threshold.

FIG. 2 combines the multi-dimensionality of the information contained in FIG. 5, presenting a condensed, easy to use graphic that describes the probability of occurrence of an icing event (PODy) and the false alarm rate (FAR) associated with a given threshold. Operationally, this tool will aid the user in selecting the appropriate threshold necessary to attain a desired/required PODy or FAR.

Figure 6:
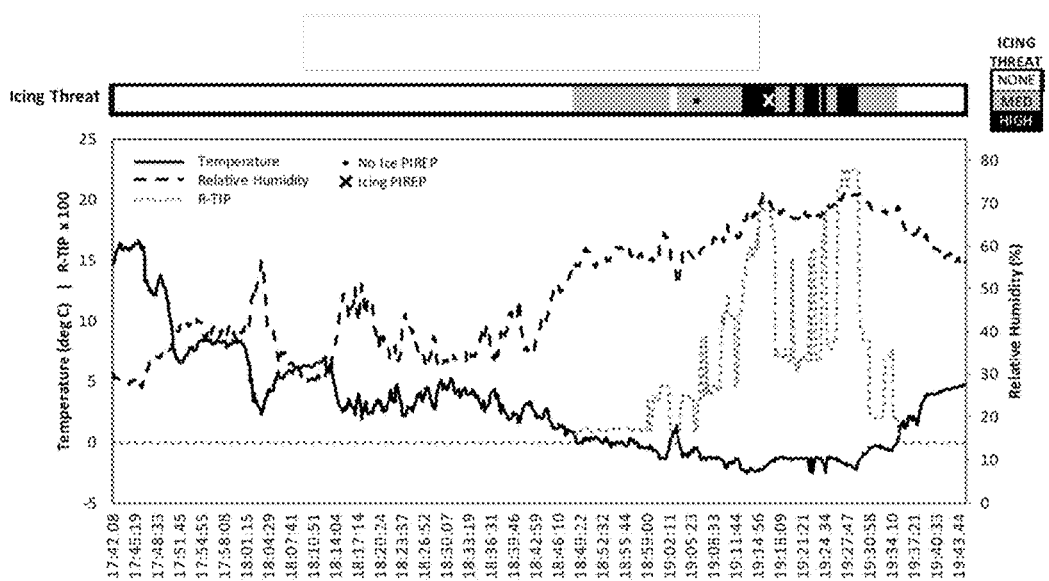
FIG. 6 is a graph of an exemplary icing threat index (ITI) calculated for a series of observed in-flight conditions (temperature and relative humidity) indicating an icing threat over time.

Turning now to FIGS. 6 and 7, exemplary ITI are graphed and portions of those ITI values are calculated in tabular form for a series of collected data where icing conditions were observed while temperature and relative humidity measurements were being taken. During this test flight, a temperature and relative humidity sensor was flown through an area of known icing, with a PIREP corroborating the occurrence; measurements were taken at a frequency of approximately once every second.

The lower portion of FIG. 6 (below the horizontal "Icing Threat" bar) presents a time series of observed parameters [temperature (solid black) and relative humidity (dashed black) along with corresponding ITI threat values output from the system. Here, non-zero ITI values coincident with times where temperatures are below freezing when sufficient moisture (as indicated by relative humidity values) is present, creating an environment with the potential for (and in some cases actual) icing conditions. Larger ITI values are indicative of greater icing threats. Translating ITI values into actionable information requires the use of a critical threshold value, one that delineates between MEDIUM and HIGH threat. For this example, a 90% detection rate was required. Using the Threshold Selection Tool (FIG. 2), a threshold value of 0.15 was determined to be the threshold value necessary to attain the desired 90% detection rate, and was used to highlight HIGH icing threat on the visual display. The False Alarm Rate associated with this threshold (again extracted from the Threshold Selection Tool) is 35%. The results of application of this threshold to the time series in the lower portion of FIG. 6 are visualized in the top portion of FIG. 6, where a NO-MEDIUM-HIGH threat is presented on the operator display.

Validating the output of this schema, two separate PIREPs are annotated on the timeline where they were reported (the black dot indicates that icing was explicitly NOT observed, while the white 'X' indicates that icing WAS observed). Here, the coincident occurrence of aircraft icing within (vice merely on the edge of) an area of highlighted threat demonstrates the ITI's value at providing advanced warning of an icing threat. A tabular subset of the data used to generate FIG. 6 is presented in FIG. 7.

Additionally, as noted above, the output from additional aircraft sensors may be incorporated into the verification processes for RTIP.

While certain configurations of structures have been illustrated for the purposes of presenting the basic structures of the present invention, one of ordinary skill in the art will appreciate that other variations are possible which would still fall within the scope of the appended claims.

The invention claimed is:

1. A system for predicting a potential icing condition for an airborne aircraft, comprising:
   a sensor interface configured to receive a temperature measurement and a relative humidity measurement from at least one sensor coupled to the airborne aircraft; and
   circuitry configured to calculate an icing threat index based on the temperature measurement and the relative humidity measurement received from the at least one sensor via the sensor interface.

2. The system as claimed in claim 1, wherein the system is housed in an autonomous airborne aircraft.

3. The system as claimed in claim 1, wherein the circuitry configured to receive and configured to calculate comprise a processor couple to non-transient digital memory, wherein the digital memory stores computer instructions implementable by the processor, the computer instructions configured to receive the temperature measurement and the relative humidity measurement from the at least one sensor coupled to the airborne aircraft and to calculate the icing threat index based on the temperature measurement and the relative humidity measurement received from the at least one sensor.

4. The system as claimed in claim 1, wherein the circuitry to calculate the icing threat index based on the temperature measurement and the relative humidity measurement received from the at least one sensor comprises circuitry for using a mathematical relationship between two tables indexed by the temperature measurement and the relative humidity measurement.

5. The system as claimed in claim 1, further comprising: circuitry to receive an output from at least one additional sensor relevant to the prediction of aircraft icing conditions, wherein the circuitry configured to calculate the icing threat index is further based the output from the at least one additional sensor relevant to the prediction of aircraft icing conditions.

6. The system as claimed in claim 1, further comprising: circuitry to receive at least one modeled parameter relevant to the prediction of aircraft icing conditions, wherein the circuitry configured to calculate the icing threat index is further based the at least one modeled parameter relevant to the prediction of aircraft icing conditions.

7. The system as claimed in claim 5, further comprising: circuitry to receive at least one modeled parameter relevant to the prediction of aircraft icing conditions, wherein the circuitry configured to calculate the icing threat index is further based the at least one modeled parameter relevant to the prediction of aircraft icing conditions.

8. The system as claimed in claim 3, wherein the computer instructions configured to receive the temperature measurement and the relative humidity measurement and to calculate the icing threat index based on the temperature measurement and the relative humidity measurement received from the at least one sensor further comprises code to receive an output from at least one additional sensor relevant to the prediction of aircraft icing conditions, and to calculate the icing threat index based on the temperature measurement, the relative humidity measurement, and the output from the at least one additional sensor relevant to the prediction of aircraft icing conditions.

9. The system as claimed in claim 3, wherein the computer instructions configured to receive the temperature measurement and the relative humidity measurement and to calculate the icing threat index based on the temperature measurement and the relative humidity measurement received from the at least one sensor further comprises code to (a) receive (1) an output from at least one additional sensor relevant to the prediction of aircraft icing conditions and (2) a modeled parameter relevant to the prediction of aircraft icing conditions, and (b) to calculate the icing threat index based on the temperature measurement, the relative humidity measurement, the output from the at least one additional sensor relevant to the prediction of aircraft icing conditions, and the modeled parameter relevant to the prediction of aircraft icing conditions.

10. The system as claimed in claim 1, wherein the circuitry configured to calculate the icing threat index based on the temperature measurement and the relative humidity measurement received from the at least one sensor comprises means for calculating the icing threat index based on the temperature measurement and the relative humidity measurement received from the at least one sensor.

11. The system as claimed in claim 10, wherein the means for calculating the icing threat index based on the temperature measurement and the relative humidity measurement received from the at least one sensor comprises at least one of (1) a system on a chip, (2) a processor and memory, (3) an ASIC, and (4) reprogrammable circuitry.

12. The system as claimed in claim 11, wherein the reprogrammable circuitry comprises at least one of a generic array of logic (GAL) or a field programmable gate array (FPGA).

13. The system as claimed in claim 10, wherein the means for calculating the icing threat index based on the temperature measurement and the relative humidity measurement received from the at least one sensor comprises fuzzy-logic circuitry for combining a first relative potential for icing associated with a temperature interest map and a second relative potential for icing associated with a temperature interest map.

14. The system as claimed in claim 13, wherein the fuzzy-logic circuitry for combining the first relative potential for icing associated with the temperature interest map and the second relative potential for icing associated with the temperature interest map comprises a multiplier.

15. The system as claimed in claim 13, wherein the fuzzy-logic circuitry for combining the first relative potential for icing associated with the temperature interest map and the second relative potential for icing associated with the temperature interest map comprises at least one of (1) a system on a chip, (2) a processor and memory, (3) an ASIC, and (4) reprogrammable circuitry.

16. The system as claimed in claim 15, wherein the reprogrammable circuitry comprises at least one of a generic array of logic (GAL) or a field programmable gate array (FPGA).

17. The system as claimed in claim 5, wherein the output from the at least one additional sensor relevant to the prediction of aircraft icing conditions comprises at least one of a vertical velocity, a cloud top temperature, a presence of super-cooled liquid water, and radar reflectivity.

18. The system as claimed in claim 5, wherein the output from the at least one additional sensor relevant to the prediction of aircraft icing conditions comprises at least one of a physical and/or thermodynamic measure of the atmosphere and its constituents.

19. The system as claimed in claim 9, wherein the output from the at least one additional sensor relevant to the prediction of aircraft icing conditions comprises at least one of a vertical velocity, a cloud top temperature, a presence of super-cooled liquid water, and radar reflectivity.

20. The system as claimed in claim 9, wherein the output from the at least one additional sensor relevant to the prediction of aircraft icing conditions comprises at least one of a physical and/or thermodynamic measure of the atmosphere and its constituents.

* * * * *